(12) United States Patent  (10) Patent No.: US 7,674,279 B2
Johnson  (45) Date of Patent: Mar. 9, 2010

(54) BONE PLATE

(75) Inventor: Jeffrey Johnson, Brandon, MS (US)

(73) Assignee: Spinal U.S.A., Pearl, MS (US)

( * ) Notice: Subject to any disclaimer, the term of this patent is extended or adjusted under 35 U.S.C. 154(b) by 196 days.

(21) Appl. No.: 11/869,159

(22) Filed: Oct. 9, 2007

(65) Prior Publication Data
US 2008/0091206 A1  Apr. 17, 2008

Related U.S. Application Data

(60) Provisional application No. 60/829,335, filed on Oct. 13, 2006.

(51) Int. Cl.
A61B 17/80 (2006.01)
(52) U.S. Cl. ......................... 606/295; 606/71
(58) Field of Classification Search ............. 606/70–71, 606/246, 279–299, 902–906
See application file for complete search history.

(56) References Cited

U.S. PATENT DOCUMENTS

| 4,074,608 | A |   | 2/1978  | Siebol |
|---|---|---|---|---|
| 4,170,920 | A |   | 10/1979 | Siebol |
| 4,580,936 | A |   | 4/1986  | Francis et al. |
| 5,163,960 | A |   | 11/1992 | Bonutti |
| 5,364,399 | A | * | 11/1994 | Lowery et al. ............... 606/295 |
| 5,405,391 | A |   | 4/1995  | Hednerson et al. |
| 5,501,695 | A |   | 3/1996  | Anspach et al. |
| 5,593,425 | A |   | 1/1997  | Bonutti et al. |
| 5,725,541 | A |   | 3/1998  | Anspach, III et al. |
| 5,735,875 | A |   | 4/1998  | Bonutti et al. |
| 5,928,267 | A |   | 7/1999  | Bonutti et al. |
| 5,951,558 | A | * | 9/1999  | Fiz ............................... 606/70 |
| 6,059,817 | A |   | 5/2000  | Bonutti et al. |
| 6,066,175 | A |   | 5/2000  | Henderson et al. |
| 6,080,161 | A |   | 6/2000  | Eaves, III et al. |
| 6,139,550 | A | * | 10/2000 | Michelson ................... 606/70 |
| 6,193,721 | B1 |  | 2/2001  | Michelson |
| 6,203,565 | B1 |  | 3/2001  | Bonutti et al. |
| 6,299,398 | B1 |  | 10/2001 | Shinjo |
| 6,342,074 | B1 |  | 1/2002  | Simpson |
| RE037,665 | E |  | 4/2002  | Ralph et al. |
| 6,383,186 | B1 |  | 5/2002  | Michelson |
| 6,398,783 | B1 |  | 6/2002  | Michelson |
| 6,406,234 | B2 |  | 6/2002  | Frigg |
| 6,428,542 | B1 |  | 8/2002  | Michelson |
| 6,432,106 | B1 |  | 8/2002  | Fraser |
| 6,454,771 | B1 |  | 9/2002  | Michelson |
| 6,464,713 | B2 |  | 10/2002 | Bonutti |
| 6,527,776 | B1 |  | 3/2003  | Michelson |
| 6,558,387 | B2 |  | 5/2003  | Errico et al. |
| 6,558,423 | B1 |  | 5/2003  | Michelson |
| 6,565,571 | B1 |  | 5/2003  | Jackowski et al. |
| 6,623,487 | B1 |  | 9/2003  | Goshert |
| 6,656,181 | B2 |  | 12/2003 | Dixon et al. |
| 6,695,845 | B2 |  | 2/2004  | Dixon et al. |

(Continued)

Primary Examiner—Thomas C Barrett
Assistant Examiner—Larry E Waggle, Jr.
(74) Attorney, Agent, or Firm—Cermak Kenealy Vaidya & Nakajima LLP; Adam J. Cermak

(57) ABSTRACT

A bone plate includes one or more locking devices which rotate to inhibit or prevent bone screws from backing out of the plate when installed on a patient. The locking devices can be in the shape of a bow tie or a capital letter I.

20 Claims, 3 Drawing Sheets

U.S. PATENT DOCUMENTS

| | | |
|---|---|---|
| 6,730,127 B2 | 5/2004 | Michelson |
| 6,740,088 B1 | 5/2004 | Kozak et al. |
| 6,764,489 B2 | 7/2004 | Ferree |
| 6,890,335 B2 * | 5/2005 | Grabowski et al. ............ 606/71 |
| 6,913,666 B1 | 7/2005 | Aeschlimann et al. |
| 6,916,320 B2 | 7/2005 | Michelson |
| 6,974,479 B2 | 12/2005 | Trieu |
| 6,984,234 B2 | 1/2006 | Bray |
| 7,041,105 B2 | 5/2006 | Michelson |
| 7,044,952 B2 | 5/2006 | Michelson |
| 7,060,069 B2 | 6/2006 | Kozak et al. |
| 7,063,701 B2 | 6/2006 | Michelson |
| 7,063,702 B2 | 6/2006 | Michelson |
| 7,074,221 B2 | 7/2006 | Michelson |
| 7,077,844 B2 | 7/2006 | Michelson |
| 7,094,239 B1 | 8/2006 | Michelson |
| 7,097,646 B2 | 8/2006 | Schantz |
| 7,104,991 B2 | 9/2006 | Dixon et al. |
| 7,118,573 B2 | 10/2006 | Michelson |
| 2002/0045896 A1 | 4/2002 | Michelson |
| 2002/0120270 A1 | 8/2002 | Trieu et al. |
| 2002/0183756 A1 | 12/2002 | Michelson |
| 2003/0060828 A1 * | 3/2003 | Michelson ................... 606/71 |
| 2004/0024464 A1 | 2/2004 | Errico et al. |
| 2004/0181229 A1 | 9/2004 | Michelson |
| 2004/0193269 A1 | 9/2004 | Fraser et al. |
| 2004/0210218 A1 | 10/2004 | Dixon et al. |
| 2004/0225290 A1 | 11/2004 | Ferree |
| 2005/0027297 A1 | 2/2005 | Michelson |
| 2005/0027298 A1 | 2/2005 | Michelson |
| 2005/0085913 A1 | 4/2005 | Fraser et al. |
| 2005/0137597 A1 * | 6/2005 | Butler et al. .................. 606/69 |
| 2005/0216009 A1 | 9/2005 | Michelson |
| 2005/0261774 A1 | 11/2005 | Trieu |
| 2005/0283152 A1 * | 12/2005 | Lindemann et al. ........... 606/61 |
| 2006/0142768 A1 | 6/2006 | Paul |
| 2006/0235400 A1 | 10/2006 | Schneider |

* cited by examiner

BONE PLATE

This application claims priority under 35 U.S.C. §119 to U.S. Provisional Application No. 60/829,335, filed 13 Oct. 2006, the entirety of which is incorporated by reference herein.

BACKGROUND OF THE INVENTION

1. Field of the Invention

The present invention relates to devices, systems, and processes useful as bone plates.

2. Brief Description of the Related Art

Anterior plates are known, including the screws that are used with such plates. A problem often experienced with such plates is that the screws back out of the bone into which it has been secured, thus jeopardizing the stability of the bone fusion. To address this problem, it has been proposed to include a locking element on the bone plate which is positionable so that the locking element physically interferes with the head of the screw, thus inhibiting the screw from backing out. For example, U.S. Pat. Nos. 6,730,127 and 6,890,335 describe locking elements for the screws in bone plates.

The prior locking elements have some disadvantages. Many of the prior locking elements are nearly entirely circular, thus increasing the weight of the bone plate. Many prior locking elements rotate only partially over the screw hole, and do not lock up against the screws. There remains a need for bone plates with bone screws for improvements which can address these and other problems.

SUMMARY

One of numerous aspects of the present invention includes a bone plate comprising a plate having a top surface and a bottom surface, at least two screw holes extending through the plate, the at least two screw holes having centers positioned apart at a distance A, a hole extending through the plate, the hole positioned generally between the at least two screw holes at a distance X from a line connecting the centers of the at least two screw holes, a rotatable locking device positioned in the hole, the rotatable locking device including first portions which extend above the plate top surface, second portions extending through the hole toward the bottom surface, and a center of rotation coincident with the center of said hole, wherein the first portions define a longest portion of length L, extending laterally from one side of said center of rotation to another side of said center of rotation, a widest portion of width $W_1$ at an end of the longest portion, and a narrowest portion of width $W_2$, adjacent said center of rotation, and wherein $L = 1 \cdot (\sqrt{R_1^2 - (R_1-T)^2})$, with $1.5 \leq 1 \leq 2.5$, $W_1 = R_1/w_1$, with $2.0 \leq w_1 \leq 2.7$, and $W_2 = R_1/w_2$, with $3.0 \leq w_2 \leq 3.7$.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
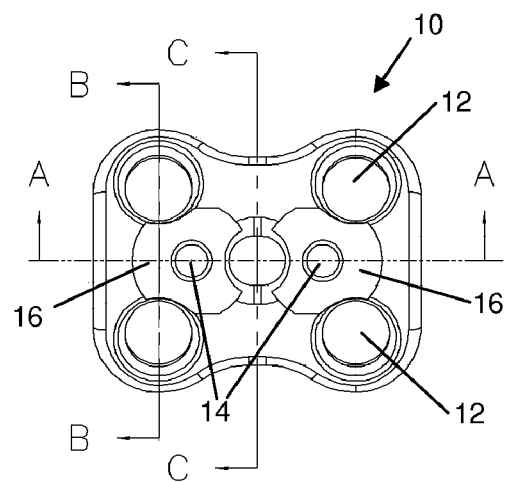
FIG. 1 illustrates a top plan view of an exemplary plate in accordance with principles of the present invention.

Referring to the drawing figures, like reference numerals designate identical or corresponding elements throughout the several figures.

FIG. 1 illustrates an exemplary anterior plate 10 embodying principles of the present invention. Anterior plate 10 is similar in some respects to prior anterior plates; portions which are similar will not be described herein so as to not obscure aspects and principles of the present invention. The plate 10 include generally curved upper and lower faces, and a plurality of screw holes 12 (the screws are not illustrated) and holes 14, both extending though the plate. The holes 14 are positioned, sized, and configured to each accept a swiveling, locking device or rivet 20, each of which is partially received in the holes 14 and within optional recesses 16 formed in the top surface of the plate. The optional recesses 16 are generally circular, except where they overlap the holes 12, 14, with a radius large enough to receive a rivet 10 therein and permit the rivet to rotate in the recess. The depth of the recesses 16, when provided, need not be constant and can be any depth that permits the rivets 20 to function as locking devices as described herein. The (unlabeled) center hole is commonly provided to permit the practitioner/doctor to see a graft placed between vertebral bodies, and is commonly referred to as a "graft window". The graft window allows the doctor to see the graft and helps the doctor align the plate accordingly.

Figure 2:
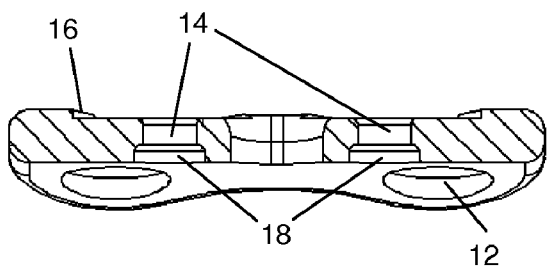
FIG. 2 illustrates a cross-sectional view of the plate of FIG. 1, taken at line A-A.
Figure 3:
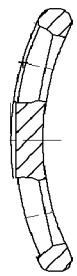
FIG. 3 illustrates a cross-sectional view of the plate of FIG. 1, taken at line B-B.
Figure 4:
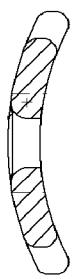
FIG. 4 illustrates a cross-sectional view of the plate of FIG. 1, taken at line C-C.
Figure 5:
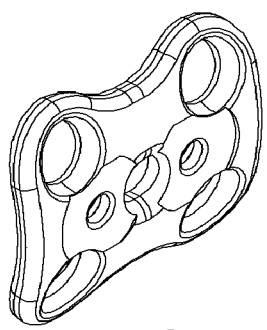
FIG. 5 illustrates a top, left, rear perspective view of the plate of FIG. 1.
Figure 6:
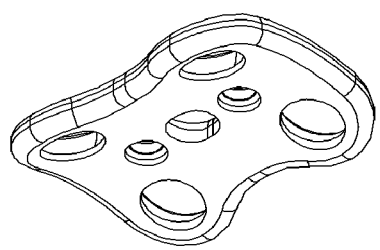
FIG. 6 illustrates a bottom, right, front perspective view of the plate of FIG. 1.

With reference to FIG. 2, which illustrates a cross-sectional view taken a line A-A in FIG. 1, the holes 14 include, on a side opposite the recesses 16, enlarged or countersunk portions 18, to receive portions of the rivets 20, as described elsewhere herein. In the exemplary embodiment illustrated herein, the enlarged portions 18 can be formed as a countersunk portion of the hole 14; however, other shapes, including frustocones and multiply-stepped countersunk holes, are also part of the present invention. FIGS. 3 and 4 show the generally curved shape of the plate 10, while FIGS. 5 and 6 show perspective views.

Figure 7:
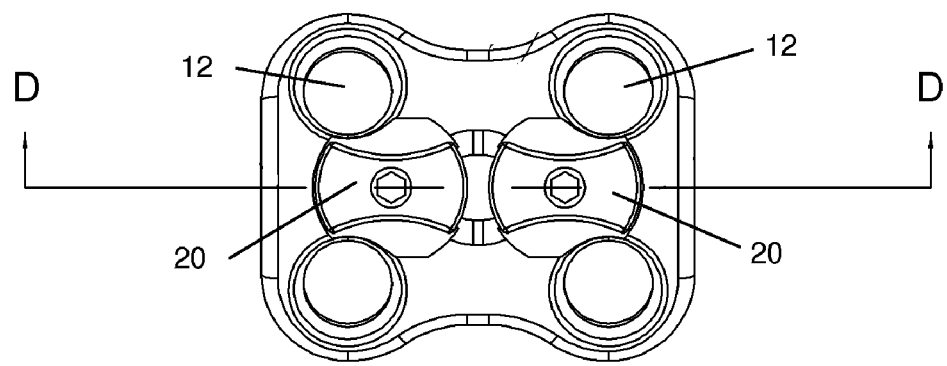
FIG. 7 illustrates a top plan view of the plate of FIG. 1, including exemplary locking rivets in accordance with principles of the present invention.
Figure 8:
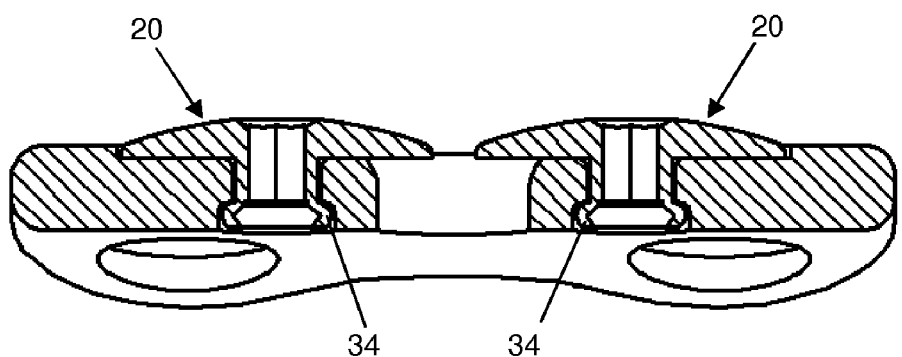
FIG. 8 illustrates a cross-sectional view of the plate of FIG. 7, taken at line D-D.
Figure 9:
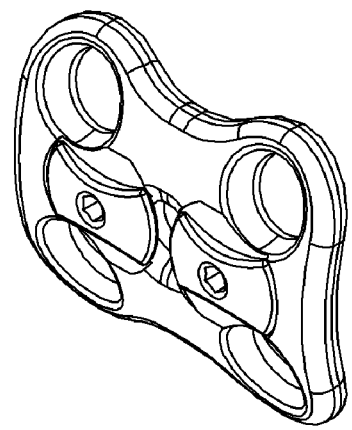
FIG. 9 illustrates a top, right, rear perspective view of the plate of FIG. 7.

With reference to FIGS. 7-9, one or more rivets 20 are positioned in the holes 14 and the recesses 16, when provided, with a tubular malleable portion 34 expanded into the enlarged portions 18 of the holes 14, thus preventing the rivets from moving out of the holes 14, while still permitting the rivets to rotate or swivel in the holes. The malleable portion 34 is advantageously an annular extension of the rivet, but may alternatively include two or more separate tines, e.g., the malleable portion can include a split annulus.

Figures 10, 11, 12:
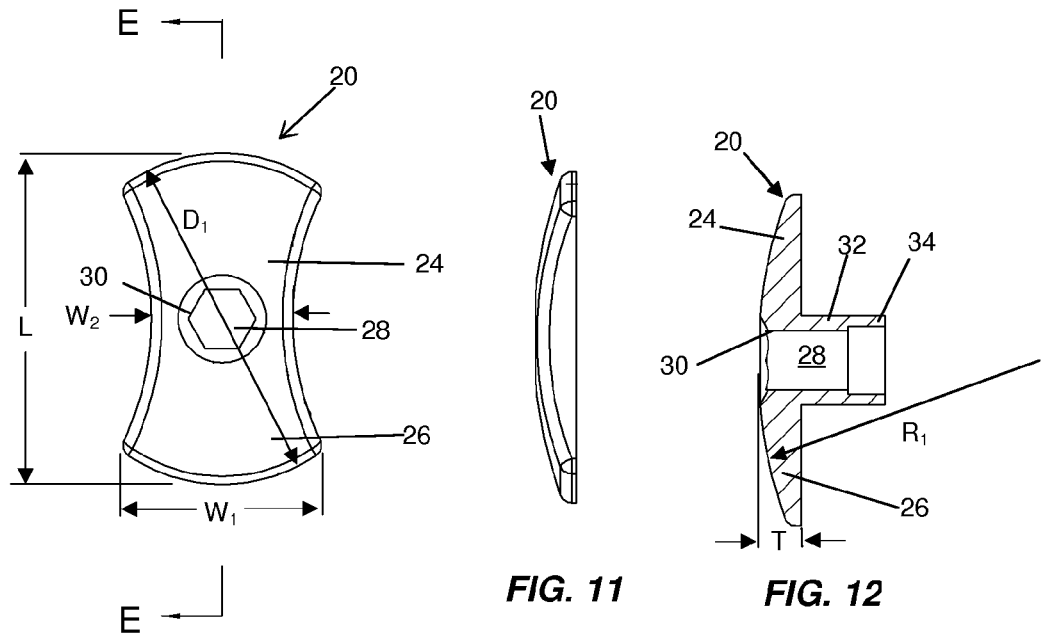
FIG. 10 illustrates a top plan view of an exemplary rivet in accordance with principles of the present invention.
FIG. 11 illustrates a side elevational view of the rivet of FIG. 10.
FIG. 12 illustrates a cross-sectional view of the rivet of FIG. 10, taken at line E-E.

FIGS. 10-12 illustrate top plan, side elevational, and cross-sectional (at line E-E in FIG. 10) views, respectively, of a rivet 20 embodying principles of the present invention. The exemplary rivet 20 is preferably generally in the shape of a 'bow tie', that is, includes convexly curved edges on opposite sides of a center hole 28, and concavely curved edges joining the convexly curved edges, the concavely curved edges being on opposite sides of the center hole. While the exemplary embodiment illustrated in the figures shows these edges to be curved, less preferred embodiments include edges that include straight portions. The rivet 20 includes one or more flanges 24, 26, sized to extend over the holes 14 and thus prevent a screw (not illustrated) from backing out of the hole 12. The rivet 20 includes a shank 32 extending from a bottom surface and a hole or bore 28 extending from the top surface and through the shank. A driving surface 30 is preferably provided on the top surface of the rivet to permit a user to rotate the rivet in the plate 10; while a hex shape is illustrated, it is but one of numerous alternative driving surfaces encompassed by the present invention, including a cylindrical shape.

The rivet's shank 32 includes a malleable portion 34 at the end of the shank opposite the flanges 24, 26. Providing the malleable portion 34 permits the rivet 20 to be secured in place in the plate 10 by crimping and expanding the malleable portion into the enlarged portion 18, when the rivet is located in a hole 14. In this manner, the rivet 20 is retained in place, while still being rotatable in the hole 14 to move the flanges 24, 26 from positions in the recesses 16 away from (FIG. 7) and over the screws in the holes 12.

It has been found that the geometries and placements of the holes 12 and the rivets 20 are interrelated, resulting in rivets that operate to inhibit, and preferably prevent, the screws in holes 12 from backing out, while still being easy to the practitioner to manipulate the rivets into a locking position. In connection with this explanation, FIGS. 10-13 have been labeled with several dimensional variables, as follows:

| Variable | Description |
| --- | --- |
| A | distance between the centers of two screw holes 12 |
| L | length of rivet |
| $R_1$ | radius of curvature of top surface of rivet |
| T | thickness of rivet head at its center |
| $W_1$ | width of widest portion of rivet |
| $W_2$ | width of narrowest portion of rivet, adjacent hole 28 |
| $D_1$ | diameter of curvature of curved outer edge of rivet |
| X | distance from the line connecting the centers of holes 12, to the center of an adjacent hole 14 |

The distance A is, particularly advantageously, first determined based on the size of the plate needed for the particular application. The distance X is then selected to minimize stress concentrations in the plate, as well understood by those of ordinary skill in the art. With A and X thus determined for a particular plate, and more specifically the configurations of the holes 12, 14 in the plate, the set of configurations of the rivet 20 embodying principles of the present invention can be determined:

$T = A/t$; $8 \leq t \leq 12$, advantageously $9 \leq t \leq 11$, more advantageously $t = 10$ $R_1 = (r) \cdot (A)$; $0.8 \leq r \leq 1.2$, advantageously $0.9 \leq r \leq 1.1$, more advantageously $r = 1.06$ $L = 1 \cdot (sqrt(R_1^2 - (R_1 - T)^2))$; $1.5 \leq l \leq 2.5$, advantageously $1.8 \leq l \leq 2.2$, more advantageously $l = 2$ $W_1 = R_1/w_1$; $2.0 \leq w_1 \leq 2.7$, advantageously $2.2 \leq w_1 \leq 2.5$, more advantageously $w_1 = 2.331$ $W_2 = R_1/w_2$; $3.0 \leq w_2 \leq 3.7$, advantageously $3.2 \leq w_2 \leq 3.5$, more advantageously $w_2 = 3.339$ $D_1 = (d_1) \cdot (W_1)$; $1.0 \leq d_1 \leq 2.0$, advantageously $1.4 \leq d_1 23 1.8$, more advantageously $d_1 = 1.633$ While the drawing figures illustrate a "bow tie" configuration of the top portion of the locking device 20, according to principles of the present invention, other exemplary embodiments are of other configurations. By way of non-limiting example, the locking device can have the shape of a capital letter "I", such that the length L corresponds to the long portion of the "I", width $W_1$ corresponds to the length of each of the two cross-members of the "I", and the width $W_2$ corresponds to the width of the long portion of the "I", with the "I" including the hole 28 at the midpoint of the long portion of the "I" and coincident with the hole 14. For such an "I"-shaped embodiment, some or all of the curved portions, described with reference to a "bow tie" embodiment, optionally can be excluded.

Figure 13:
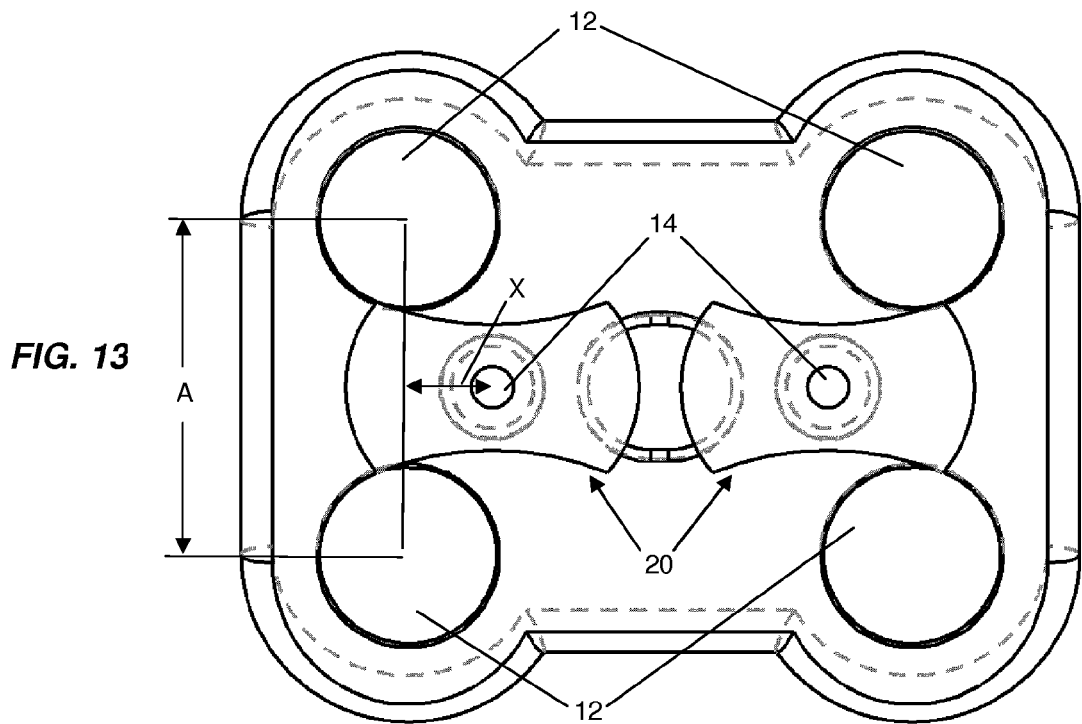
FIG. 13 illustrates an enlarged top plan view of another exemplary embodiment of a plate in accordance with the present invention.

Additionally, the dimension $W_1$ is optionally, yet advantageously, selected with the radii of the holes 12, their mutual spacing A, and the distance X, so that the locking device 20 can be oriented relative to the holes 12 so as to not overlap either of the holes, that is, as illustrated in FIG. 13, so that both of the screws (not illustrated) for locking device 20 can be inserted into a hole 12 and thereafter simultaneously locked in the hole.

Example I

All Dimensions in mm

| | |
| --- | --- |
| A | 9.47 |
| T | 0.947 |
| R1 | 10.0382 |
| L | 98.512471 |
| W1 | 4.306392 |
| W2 | 3.006349 |
| D1 | 7.032338 |

Example II

All Dimensions in mm

| | |
| --- | --- |
| A | 11.58 |
| T | 1.158 |
| R1 | 12.2748 |
| L | 10.40913 |
| W1 | 5.265894 |
| W2 | 3.67619 |
| D1 | 8.599206 |

Preferably, the plate and rivets are made out of the same or different biocompatible materials, e.g., a titanium alloy, stainless steel, and the like; alternatively, a bioresorbable material can be used. The present invention is not restricted to a particular number of holes and screws in the plate, as such plates are made in different lengths to fit the patient's anatomy. By way of non-limiting examples, the plates can be 4-hole, 6-hole, 8-hole, and 10-hole plates. Each set of two holes 12, the screws for which are lockable by a common rivet 20, are separated by a distance which is greater than the distance A, so that the rivet 20 for each set of holes 12 does not interfere with the rivet for the other set of holes.

Preferably, a 4-hole plate will have two rivets, one for two holes, but one rivet per hole is also within the scope of the present invention. Further preferably, the rivet 20 is provided with a bottom surface which increases the friction between the rivet and the plate and/or screw, as the rivet turns into the lock position. Since the rivet 20 is crimped into the plate 10, the rivet will not come out of the hole 14. The rivet 20 is not restricted to the particular bow tie shape illustrated herein. Alternatively, the rivet 20 can be oval, round, square, rectangular, or any other shape which permits it to physically impede the screw from backing out of the plate 10. Furthermore, the present invention is not limited to plates used as anterior plates, and extends to any bone applications, e.g., long bones, short bones, vertebral body bones, and the like.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

I claim:

1. A bone plate comprising:
  a plate having a top surface and a bottom surface;
  at least two screw holes extending through the plate, the at least two screw holes having centers positioned apart at a distance A;
  a hole extending through the plate, the hole positioned generally between the at least two screw holes at a distance X from a line connecting the centers of the at least two screw holes;
  a rotatable locking device positioned in the hole, the rotatable locking device including first portions which extend above the plate top surface, second portions extending through the hole toward the bottom surface, and a center of rotation coincident with the center of said hole;
  wherein the first portions define
    a longest portion of length L, extending laterally from one side of said center of rotation to another side of said center of rotation,
    a curved top surface having a radius of curvature $R_1$,
    a thickness T at said center of rotation,
    a widest portion of width $W_1$ at an end of the longest portion, and
    a narrowest portion of width $W_2$, adjacent said center of rotation; and
  wherein
    $L = 1 \cdot (\text{sqrt}(R_1^2 - (R_1-T)^2))$, with $1.5 \leq 1 \leq 2.5$,
    $W_1 = R_1/w_1$, with $2.0 \leq w_1 \leq 2.7$, and
    $W_2 = R_1/w_2$, with $3.0 \leq w_2 \leq 3.7$.

2. A bone plate according to claim 1, wherein $1.8 \leq 1 \leq 2.2$.

3. A bone plate according to claim 1, wherein $1=2$.

4. A bone plate according to claim 1, wherein $2.2 \leq w_1 \leq 2.5$.

5. A bone plate according to claim 1, wherein $w_1=2.331$.

6. bone plate according to claim 1, wherein $3.2 \leq w_2 \leq 3.5$.

7. bone plate according to claim 1, wherein $w_2=3.339$.

8. A bone plate according to claim 1, wherein the first portions define a curved outer edge at said longest portion having a diameter of curvature $D_1$, $D_1=(d_1) \cdot (W_1)$, and $1.0 \leq d_1 \leq 2.0$.

9. A bone plate according to claim 8, wherein $1.4 \leq d_1 \leq 1.8$.

10. A bone plate according to claim 8, wherein $d_1=1.633$.

11. A bone plate according to claim 1, wherein $T=A/t$, with $8 \leq t \leq 12$.

12. A bone plate according to claim 11, wherein $9 \leq t \leq 11$.

13. A bone plate according to claim 11, wherein $t=10$.

14. A bone plate according to claim 1, wherein $R_1=(r) \cdot (A)$, with $0.8 \leq r \leq 1.2$.

15. A bone plate according to claim 14, wherein $0.9 \leq r \leq 1.1$.

16. A bone plate according to claim 14, wherein $r=1.06$.

17. A bone plate according to claim 1, wherein the first portions are generally in the shape of a bow tie.

18. A bone plate according to claim 1, wherein the first portions are generally in the shape of a capital letter I.

19. A bone plate according to claim 1, wherein said hole includes a countersunk portion extending from said bone plate bottom surface, and said locking device second portions include a malleable portion extending laterally into said countersunk portion.

20. A bone plate according to claim 1, wherein $W_1$, the radii of the screw holes, the distance A, and the distance X, are mutually selected so that there is a rotated position of the first portions at which the first portions do not overlap the screw holes.

* * * * *